United States Patent
Naqvi et al.

(10) Patent No.: US 9,220,903 B2
(45) Date of Patent: Dec. 29, 2015

(54) OPTIMIZATION OF PACEMAKER SETTINGS WITH R-WAVE DETECTION

(71) Applicant: AtCor Medical Pty Ltd, West Ryde, NSW (AU)

(72) Inventors: Tasneem Z. Naqvi, Los Angeles, CA (US); Dean C. Winter, Helotes, TX (US)

(73) Assignee: AtCor Medical Pty, Ltd. (AU)

( * ) Notice: Subject to any disclaimer, the term of this patent is extended or adjusted under 35 U.S.C. 154(b) by 0 days.

(21) Appl. No.: 14/571,884

(22) Filed: Dec. 16, 2014

(65) Prior Publication Data

US 2015/0165211 A1 Jun. 18, 2015

Related U.S. Application Data (60) Provisional application No. 61/916,508, filed on Dec. 16, 2013.

(51) Int. Cl.
*A61N 1/36* (2006.01)
*A61N 1/365* (2006.01)
(Continued)

(52) U.S. Cl.
CPC ........ *A61N 1/36585* (2013.01); *A61B 5/02028* (2013.01); *A61B 5/0452* (2013.01); *A61N 1/3684* (2013.01); *A61N 1/36564* (2013.01)

(58) Field of Classification Search
CPC ........... A61B 5/02028; A61N 1/36564; A61N 1/36585; A61N 1/3684
See application file for complete search history.

(56) References Cited

U.S. PATENT DOCUMENTS

| | | |
|---|---|---|
| 4,094,308 A | 6/1978 | Cormier |
| 5,088,491 A | 2/1992 | Schaldach |

(Continued)

FOREIGN PATENT DOCUMENTS

| | | |
|---|---|---|
| EP | 1055395 | 11/2000 |
| EP | 2070472 | 6/2009 |

(Continued)

OTHER PUBLICATIONS

SphygmoCor at the Heart of Cardiovascular Management, Operator's Manual, AtCor Medical, Copyright 2006, pp. 1-55.

(Continued)

*Primary Examiner* — Amanda Patton
(74) *Attorney, Agent, or Firm* — Andrus Intellectual Property Law, LLP (57) ABSTRACT

The system provides information to facilitate efficient optimization of programmer settings for cardiac pacemakers. It simultaneously measures a patient's electrocardiogram and peripheral blood pressure (or volumetric displacement) waveform in order to calculate, in real-time and non-invasively, a value correlated to the pre-ejection time (PET) and, optionally, ejection duration (ED) for the patient's left ventricle. The peripheral pulse waveform can be monitored with a wrist mounted tonometer, or a suitable brachial cuff device. The time difference between the occurrence of the R-wave on the ECG trace and the foot of the pulse on the radial blood pressure waveform is defined as a surrogate pre-ejection time interval (SPET). Data including the electrocardiogram and peripheral pulse trace, as well as the calculated, surrogate pre-ejection time interval (SPET) for each heart beat and trending is displayed on a computer monitor, thereby allowing a physician or nurse to quickly optimize PET for the patient and adjust programmer settings for an implanted pacemaker.

27 Claims, 7 Drawing Sheets

(51) Int. Cl.
*A61N 1/368* (2006.01)
*A61B 5/02* (2006.01)
*A61B 5/0452* (2006.01)

(56) References Cited

U.S. PATENT DOCUMENTS

| | | |
|---|---|---|
| 5,265,011 A | 11/1993 | O'Rourke |
| 5,392,780 A | 2/1995 | Ogino et al. |
| 5,487,752 A | 1/1996 | Salo et al. |
| 6,247,474 B1 | 6/2001 | Greeninger et al. |
| 6,334,849 B1 | 1/2002 | Sunagawa |
| 6,485,431 B1 | 11/2002 | Campbell |
| 6,647,287 B1 | 11/2003 | Peel, III et al. |
| 6,743,179 B2 | 6/2004 | Narimatsu et al. |
| 6,772,008 B2 | 8/2004 | Zhu et al. |
| 6,792,308 B2 | 9/2004 | Corbucci |
| 6,843,773 B2 | 1/2005 | Freund et al. |
| 8,065,002 B2 | 11/2011 | Arand et al. |
| 8,568,440 B2 | 10/2013 | Chen et al. |
| 2003/0220584 A1 | 11/2003 | Honeyager et al. |
| 2005/0027323 A1 | 2/2005 | Mulligan et al. |
| 2006/0068452 A1 | 3/2006 | Goldknopf et al. |
| 2006/0115856 A1 | 6/2006 | Goldknopf et al. |
| 2006/0115867 A1 | 6/2006 | Goldknopf et al. |
| 2006/0155202 A1 | 7/2006 | Arand et al. |
| 2006/0278532 A1 | 12/2006 | Goldknopf et al. |
| 2007/0017809 A1 | 1/2007 | Goldknopf et al. |
| 2007/0042429 A1 | 2/2007 | Goldknopf et al. |
| 2008/0195168 A1 | 8/2008 | Arand et al. |
| 2008/0287793 A1 | 11/2008 | Hoffmann |
| 2008/0289964 A1 | 11/2008 | Goldknopf et al. |
| 2009/0061457 A1 | 3/2009 | Goldknopf et al. |
| 2009/0287097 A1 | 11/2009 | Lowe |
| 2010/0241013 A1 | 9/2010 | Hatib |
| 2011/0237961 A1 | 9/2011 | Voss et al. |

FOREIGN PATENT DOCUMENTS

| | | |
|---|---|---|
| GB | 2089999 | 6/1982 |
| WO | 2007/053868 | 5/2007 |
| WO | 2010/002250 | 1/2010 |
| WO | 2010/058169 | 5/2010 |

OTHER PUBLICATIONS

Rafique, AM and Naqvi, TZ, "Novel Method for Biventricular Pacemaker Optimization by a Radial Artery Tonometer. The Case Report," Minerva Cardioangiol, Jun. 2007, 55(3):385-9.

Naqvi, TZ and Rafique, AM, "Echocardiography—guided pacemaker optimization and radial artery tonometry," J Card Failure 14(7):583-589, 2008.

Wassertheurer, W. et al, "A New Oscillometric Method for Pulse Wave Analysis: Comparison with a Common Tonometric Method," Journal of Human Hypertension (2010) 24, pp. 498-504, published online Mar. 18, 2010.

Roman, Mary J MD, et al., "High Central Pulse Pressure is Independently Associated with Adverse Cardiovascular Outcome," Journal of American College of Cardiology, vol. 54, No. 18, Oct. 27, 2009, pp. 1730-1734.

McEniery, Carmel, et al., "Central Pressure, Variability and Impact of Cardiovascular Risk Factors, The Anglo-Cardiff Collaborative Trial II," Hypertension, Jun. 2008, pp. 1476-1482.

Williams, Bryan MD, et al., "Differential Impact of Blood Pressure-Lowering Drugs on Central Aortic Pressure and Clinical Outcomes, Principal Results of the Conduit Artery Function Evaluation (CAFE) Study," Circulation, Mar. 7, 2006, pp. 1213-1225.

Pauca, Alfredo L., et al., "Prospective Evaluation of a Method of Estimating Ascending Aortic Pressure from the Radial Artery Pressure Waveform," Hypertension, Oct. 2001, vol. 38, pp. 932-937.

Sharman, James E. et al., "Validation of a Generalized Transfer Function to Noninvasively Derive Central Blood Pressure During Exercise," Hypertension, Jun. 2006, vol. 47, pp. 1203-1208.

OPTIMIZATION OF PACEMAKER SETTINGS WITH R-WAVE DETECTION

FIELD OF THE INVENTION

The invention relates to the optimization of programmable settings for cardiac pacemakers. It uses simultaneous measurement a patient's electrocardiogram (ECG) and peripheral blood pressure waveform in order to calculate, in real-time, a value correlated to the pre-ejection time (PET) for the patient's left ventricle. More specifically, the time between the detection of the R-wave in an ECG trace and the detection of the foot of the pressure pulse in the peripheral pressure waveform is calculated and displayed, and available to be used by a physician or nurse to quickly optimize PET for the patient when adjusting programmable settings for an implanted pacemaker. The system is also able to determine ejection duration (ED) for the patient's left ventricle.

BACKGROUND

A biventricular pacemaker is a type of cardiac pacemaker that can pace both the right and the left ventricle (typically the lateral wall of the left ventricle). By pacing both right and left ventricles, the pacemaker is able to resynchronize a heart whose opposing walls and right and left ventricles do not contract in synchrony. Biventricular pacemakers have at least two leads, one in the right ventricle to stimulate the septum, and the other inserted through the coronary sinus to pace the lateral wall of the left ventricle. There is typically also a lead in the right atrium to facilitate synchrony with atria contraction. The use of a biventricular pacemaker is generally referred to as cardiac resynchronization therapy (CRT).

Programmable biventricular pacemakers enable optimization of the various time delays between pacemaker timing pulses. This optimization procedure requires the physician or nurse to set delays between the various timing pulses. Its general purpose is to coordinate contraction of the various chambers in the heart to improve overall efficiency and function. The onset of electrical cardiac activity in an electrocardiogram is marked by the onset of the QRS complex and corresponds to the initial impulse time ($T_o$) for the contracting ventricle. The time from the onset of the Q-wave to the closure of the mitral valve is termed electromechanical delay (EMD). The isovolumetric contraction time interval (IVCT) begins when the mitral valve closes and ends when the blood pressure within the left ventricle is sufficient to open the aortic valve. The combination of EMD and IVCT is referred to in the art as the pre-ejection time interval (PET), and is a particularly useful parameter for CRT optimization. Typically, the attending physician will want to minimize PET.

One method of optimizing settings in programmable cardiac pacemakers is disclosed in U.S. Pat. No. 8,112,150, entitled "Optimization of Pacemaker Settings", incorporated herein by reference and assigned to the Assignee of the present application, AtCor Medical Pty. Ltd. The invention in Assignee's '150 patent uses simultaneous measurement of a patient's electrocardiogram (ECG) and a patient's peripheral blood pressure waveform in order to calculate, in real-time and non-invasively, a value correlated to the pre-ejection time (PET) for the patient's left ventricle. This value is termed a surrogate pre-ejection time (SPET) and its calculation and display enables a physician or nurse to quickly optimize PET by adjusting the programmable settings for the implanted pacemaker. To be more specific, in the system disclosed in the '150 patent, the electrocardiogram is analyzed for each pulse to determine the exact time ($T_0$) corresponding to the onset of the QRS complex or, alternatively, the time that the Q-wave reaches its minimum value as an approximation to the onset of the QRS complex. The system also measures the patient's radial pressure pulse using for example a tonometer at the wrist. The opening of the aortic valve is marked by an abrupt rise of pressure in the aorta which results in a pressure pulse waveform rising to a peak systolic pressure and then declining. The arrival of the foot of the pressure waveform at the peripheral artery, e.g. a radial artery, is delayed by a transit time (K) for the pressure wave to travel from the aorta to the peripheral artery. For any individual patient, the travel distance for the pressure wave from the aorta to the peripheral location remains constant when the patient is at rest during the CRT optimization session, as long as the peripheral pressure is measured at a fixed location (e.g. at a fixed location on the user's wrist to the measure the pressure waveform at the radial artery). As noted in the '150 patent, testing indicates that the assumption that the pulse wave velocity for the patient remains constant over the time frame required for CRT optimization is quite accurate as long as the patient remains at rest. In the '150 patent, the time interval between Q-wave ($T_0$) in the electrocardiogram and the foot ($T_2$) of the peripheral pressure wave, when the ECG trace and radial waveform are measured simultaneously, represents the actual pre-ejection time interval (PET) plus a fixed value (K), which are combined as described in the '150 patent to calculate a surrogate pre-ejection time (SPET). Since there is a constant offset (K) between the actual PET and the surrogate SPET, the doctor or nurse can optimize the pacemaker settings to minimize the actual pre-ejection time PET by minimizing the surrogate SPET.

SUMMARY OF THE INVENTION

It has been discovered that using the time of the R-wave peak in the QRS complex to calculate a surrogate pre-ejection time interval (SPET) rather than using the onset of the Q-wave or the minimum value of the Q-wave as taught in the '150 patent, normally provides more reliable and robust results. The R-wave peak is easier to detect than the Q-wave and is more stable than the Q-wave from pulse to pulse. Some of the difficulty of accurately identifying the Q-wave on a reliable basis has to do with signal noise. The amplitude of the R-wave is substantially greater than the amplitude of the Q-wave so this difficulty is mitigated somewhat when detecting the R-wave peak. Another potentially more serious problem with detecting the Q-wave is shape of the Q-wave absent noise. For example, a pathological Q-wave may have multiple peaks (minimum values), such as when ventricular contraction is disjointed. Alternatively, even in situations where the Q-wave appears to be visually clear, the trace signal may have a mathematical peak that is distinct from the visually apparent peak. If the detection of an improper Q-wave peak occurs, it can distort the calculated average SPET.

Accordingly, in one aspect, the invention is directed to a method in which a patient's electrocardiogram (ECG) is measured and, simultaneously, a blood pressure sensor is used to measure the patient's peripheral pulse waveform, e.g., with a tonometer or a brachial cuff. For each respective pulse, the electrocardiogram is analyzed to determine a time correlating to the R-wave, preferably the peak of the R-wave, and this time is defined as an R-wave impulse time ($T_R$) for the contracting ventricle. The time ($T_2$) corresponding to the realization of systolic onset in the detected peripheral pulse waveform is also determined for each respective pulse. In the preferred embodiment of the invention, time $T_2$ corresponding to the onset of systole in the measured peripheral pulse waveform is determined by analyzing the first derivative of the peripheral pulse waveform and identifying a first negative to positive zero crossing preceding a maximum value for the first derivative. In accordance with the invention, the time values $T_R$ and $T_2$ are used to calculate a surrogate pre-ejection time interval (SPET) for the pulse. This information (SPET), and trends of this information, can be used conveniently by a medical staff in order to optimize CRT adjustments.

In another aspect, the invention pertains to a system which includes hardware components and software tools that are particularly well suited to conveniently assist medical staff during CRT optimization by providing information relating to the patient's surrogate pre-ejection time (SPET). The preferred system uses much of the same hardware that is currently available in a SphygmoCor® system, utilizing an MM3™ digital signal processing electronic module. The leads from ECG electrodes are connected to the electronics module as is the cable from a blood pressure sensor, such as a tonometer. The preferred tonometer, as mentioned above, is strapped to the patient's wrist in a fixed location while the attending staff conducts CRT optimization. Analog data is sent from the electronics module to an A/D converter and the resulting digital data is analyzed and displayed via a programmed personal computer. Software on the personal computer preferably displays traces of the electrocardiogram data and the peripheral pressure waveform data as a function of time, and in real-time. The software allows the attending staff to select a given series of data representing a series of heart beats for which the surrogate pre-ejection time (SPET) is calculated for each pulse. The system preferably displays the data for each heart beat as well as an average and standard deviation for the selected series of heart beats. The system also allows the user to store data for later analysis. Typically, attending staff would adjust settings for the programmable pacemaker during CRT optimization, and compare SPET data from a previous setting to the current setting in an attempt to optimize (e.g. minimize) SPET. If desired, the system can also calculate and display other additional parameters as well. For example, as an optional feature, the system determines and displays ejection duration (ED) calculated from the peripheral pulse waveform, as is known in the art.

Further objects, features and advantages of the invention will be apparent from the following drawings and detailed description thereof.

BRIEF DESCRIPTION OF THE DRAWINGS

FIG. 4 is a graphical screen display similar to that shown in FIG. 3, however, FIG. 3 is intended to represent an example of data displayed prior to CRT optimization, whereas FIG. 4 is intended to represent data displayed after CRT optimization.

FIG. 6 is a representative screen display on a personal computer in a system implementing another aspect of the invention. In FIG. 6, the Q-wave in the displayed ECG trace is less distinct than in FIGS. 4 and 5.

DETAILED DESCRIPTION OF THE DRAWINGS

Figure 1:
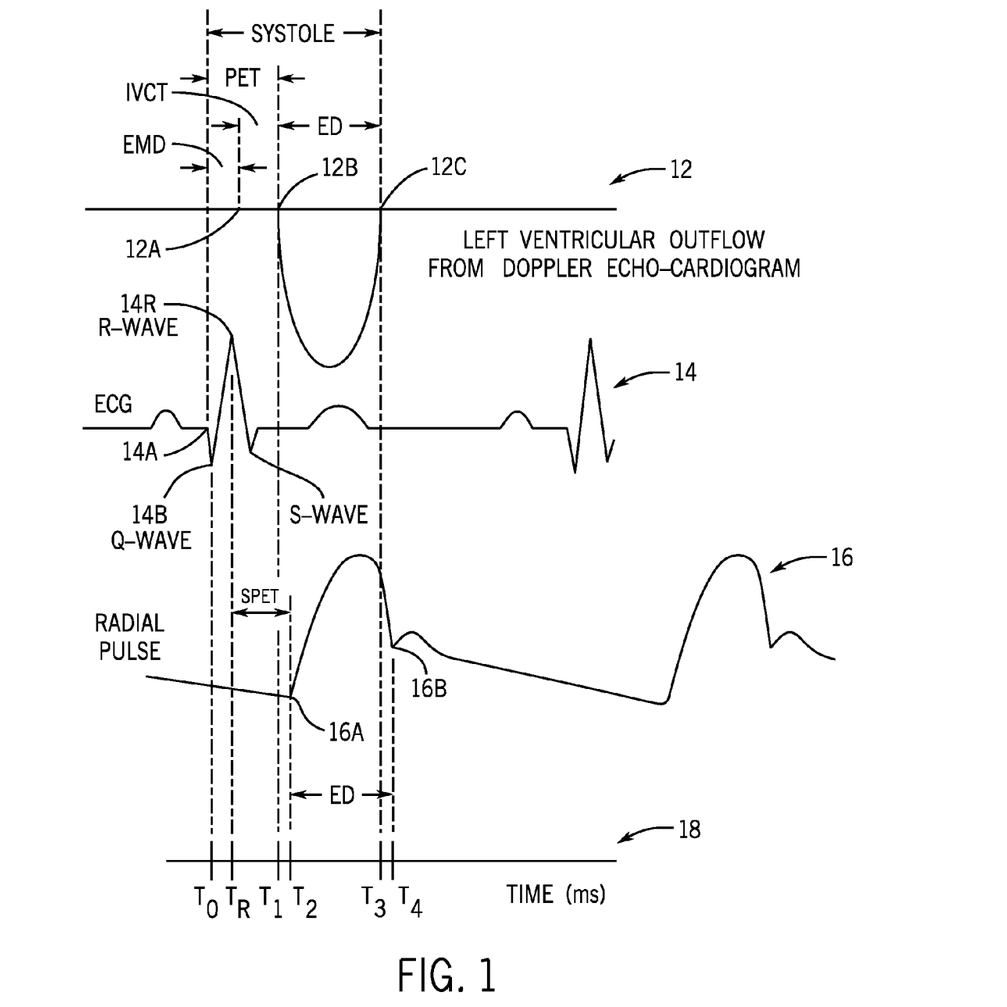
FIG. 1 is a schematic diagram illustrating blood flow through a patient's left ventricle as well as a corresponding typical electrocardiogram, and radial artery pressure pulse waves.

FIG. 1 is a schematic plot 10 with a variety of illustrative data relating to a hypothetical patient's cardiac cycle. In FIG. 1, curve 12 illustrates the outflow of blood from the patient's left ventricle as a function of time measured via a Doppler echo-cardiogram. Curve 14 represents an electrocardiogram trace (ECG). The width of the QRS complex in the electrocardiogram trace 14 is exaggerated to facilitate the explanation of the invention. Curve 16 in FIG. 1 is a peripheral pulse waveform, for example a waveform of the pressure pulse taken at the patient's radial artery. In accordance with the invention, the patient's electrocardiogram 14 and radial pulse waveform 16 are measured simultaneously. The horizontal axis at the bottom of FIG. 1 represents time in milliseconds. A typical cycle for a heart beat might take one second or one thousand milliseconds.

Generally speaking, a full cardiac cycle is divided into systole, which corresponds to contraction of the ventricles, and diastole which corresponds to the relaxation of the ventricles. In general terms, systole includes a pre-ejection time (PET) interval, and an ejection duration (ED), which is the amount of time that the aortic valve is open during the cycle. The pre-ejection time (PET) consists of electromechanical delay (EMD) which is typically defined as the time interval from the onset of the Q-wave 14A in the electrocardiogram 14 to the onset of physical cardiac contraction 12A ($T_1-T_0$), plus the isovolumetric contraction time (IVCT), which is the initial period of ventricular contraction after the mitral valve closes but before the aortic valve opens. In accordance with an embodiment of the present invention, the system detects the peak value 14R of the R-wave in the electrocardiogram 14. This time is designated as $T_R$ on axis 18 in FIG. 1. As is illustrated by curve 12, there is no blood outflowing from the left ventricle during isovolumetric contraction (IVCT). As the pressure within the left ventricle increases during isovolumetric contraction, the pressure eventually opens the aortic valve and blood flows from the left ventricle into the aorta, as indicated by reference number 12B. The time at which the aortic valve opens and blood begins to flow from the left ventricle, reference number 12B, is designated in FIG. 1 as $T_1$ along the time axis 18. FIG. 1 does not illustrate the pressure waveform in the central aorta, but if such waveform were available, the time $T_1$ would correspond to the foot of the central aortic pulse waveform, and the time interval $T_1-T_0$ would directly represent the pre-ejection time (PET) interval. However, FIG. 1 illustrates a radial pulse waveform 16 (which is measured non-invasively), not a central aortic pressure waveform. The foot 16A of the systolic portion of the radial pulse waveform occurs at time $T_2$, which is delayed and later in time than $T_1$, see time axis 18. Nevertheless, as long as the patient's peripheral pulse waveform is measured at a fixed location, such as a fixed location on the patient's wrist, the time interval $T_2-T_1$ is a constant value (K).

It has been found in many circumstances that detecting $T_R$ corresponding to the peak of the R-wave is more robust and stable over repeated cycles than attempting to accurately measure the onset of the Q-wave or the time of the Q-wave peak ($T_0$). Therefore, even though $T_R$ does not correspond to the onset of the Q-wave, detecting $T_R$ and defining the time interval $T_2-T_R$ as a surrogate pre-ejection time (SPET) has been found to be more accurate and reliable in some circumstances than detecting $T_0$ and defining SPET=$T_2-T_0$ as defined in the incorporated U.S. Pat. No. 8,112,150. The detection of the R-wave peak can be accomplished in a number of ways; including identification of the time ($T_R$) corresponding to the numerical peak value once a certain threshold has been surpassed. If a double peak is detected, $T_R$ should be defined by the first identified R-wave peak. Detection of the Q-wave minimum, e.g. in the system of incorporated U.S. Pat. No. 8,112,150, can be accomplished by analyzing the data back in time from the identified R-wave peak to find the time corresponding to a minimum value. In some cases, detecting the minimum Q-wave value can be difficult because the Q-wave amplitude can be significantly less than R-wave amplitude, and the resolution of the signal is also substantially less. This means that signal noise is more likely to lead to inaccuracies. It also means that pathogenic ventricular contractions can cause Q-wave shapes that are difficult to analyze numerically. Therefore, in accordance with the invention, the time corresponding to the R-wave ($T_R$) can be used to determine SPET.

The invention can determine the time $T_2$ (i.e. the foot 16A of the peripheral pulse wave) in the manner disclosed in U.S. Pat. No. 5,265,011 to O'Rourke, entitled "Method For Ascertaining The Pressure Pulse And Related Parameters in The Ascending Aorta From The Contour Of The Pressure Pulse In The Peripheral Arteries" issuing on Nov. 23, 1993, which is herein incorporated by reference; namely, by analyzing the first derivative of the peripheral pulse waveform and identifying the first negative to positive zero crossing preceding the maximum value for the first derivative.

The ejection duration (ED) of the left ventricle is completed when the left ventricle begins to relax and the aortic valve closes. Reference number 12C identifies the time ($T_3$) in which the aortic valve closes on curve 12. Referring now again to the peripheral pulse waveform 16, the waveform includes an incisura 16B, which is a high frequency notch in the waveform 16 resulting from the closure of the aortic valve. Time $T_4$ on the time axis 18 corresponds to the realization of the incisura 16B in the peripheral pulse waveform 16. While the form of the peripheral pulse waveform 16 is shifted or delayed in time with respect to the central aortic pressure pulse, and also very likely takes on a somewhat different form, see incorporated U.S. Pat. No. 5,265,011, the time interval from the foot 16A of the peripheral pulse wave to the incisura 16B (i.e., $T_4-T_2$=ED) corresponds accurately to the ejection duration (ED) defining the time interval between the opening 12A of the aortic valve and the closing 12B of the aortic valve. The preferred manner of detecting the location of the incisura 16B in the peripheral pulse wave 16 is disclosed in the above incorporated U.S. Pat. No. 5,265,011; namely, by taking the third derivative of the peripheral pressure waveform and identifying the first positive to negative zero crossing following the largest maximum after a second shoulder in the peripheral pressure waveform unless a second shoulder cannot be identified, in which case the first positive to negative zero crossing following the largest maximum point of the third derivative after the first shoulder.

Figure 2:
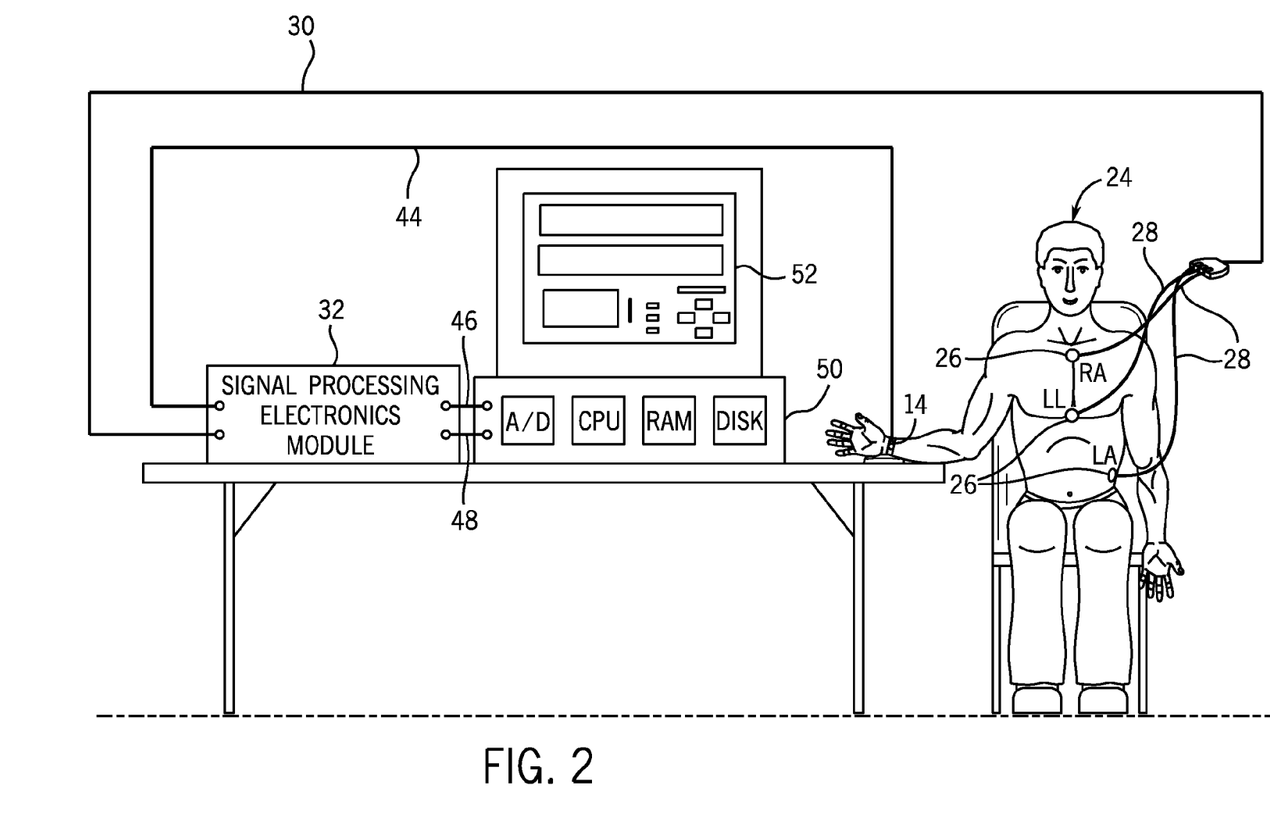
FIG. 2 is a schematic drawing illustrating a system constructed in accordance with an embodiment of the invention.

FIG. 2 is a schematic drawing illustrating the use of the invention. The patient 24 has been prepared to undergo CRT optimization, although the wand and the external CRT programming electronics are not shown for the sake of simplicity. Electrocardiogram electrodes 26 are placed on the patient's chest, as is known in the art. Alternatively, the electrodes can be placed on the peripheral limbs, as also is known in the art. Leads 28 from the electrodes 26 are connected to an ECG cable 30 which in turn is connected to a signal processing electronics module 32. As mentioned, the preferred signal processing electronics module 32 is the SphygmoCor® MM3, manufactured by AtCor Medical. As is known in the art, the electrode leads 28 and cable 30 need to be compatible with the signal processing electronics module 32. In one embodiment of the invention, a tonometer 34 monitors the patient's radial artery pressure waveform. A conventional hand-held tonometer from AtCor Medical is suitable for carrying out the invention, although it is preferred that the tonometer 34 be strapped to the wrist of the patient 24 in order to ensure that the radial pressure pulse wave be taken at a fixed location on the patient's limb during the CRT optimization session. If desired, the patient's peripheral pulse waveform can be taken at another location, for example, a brachial artery volumetric displacement waveform can be measured using an upper arm cuff. See, e.g., U.S. patent application Ser. No. 13/101,193, entitled Brachial Cuff, filed May 5, 2011, by Ahmad Qasem and assigned to the assignee of the present application, which is hereby incorporated by reference. The criterion for selecting the type of measured waveform is the ability to identify the foot of the waveform (e.g. 16A in FIG. 1). In any event, it is important that the location of the peripheral pulse waveform be measured at a fixed location during the CRT optimization session in order to ensure that the pressure pulse travel time from the aortic valve to the peripheral measurement location (e.g., wrist, or upper arm) is consistent. Since the invention relies on the simultaneous measurement of an electrocardiogram and a peripheral pulse waveform, the accuracy of the invention depends in large part on the measuring of the peripheral pulse waveform at a fixed location.

Figure 5:
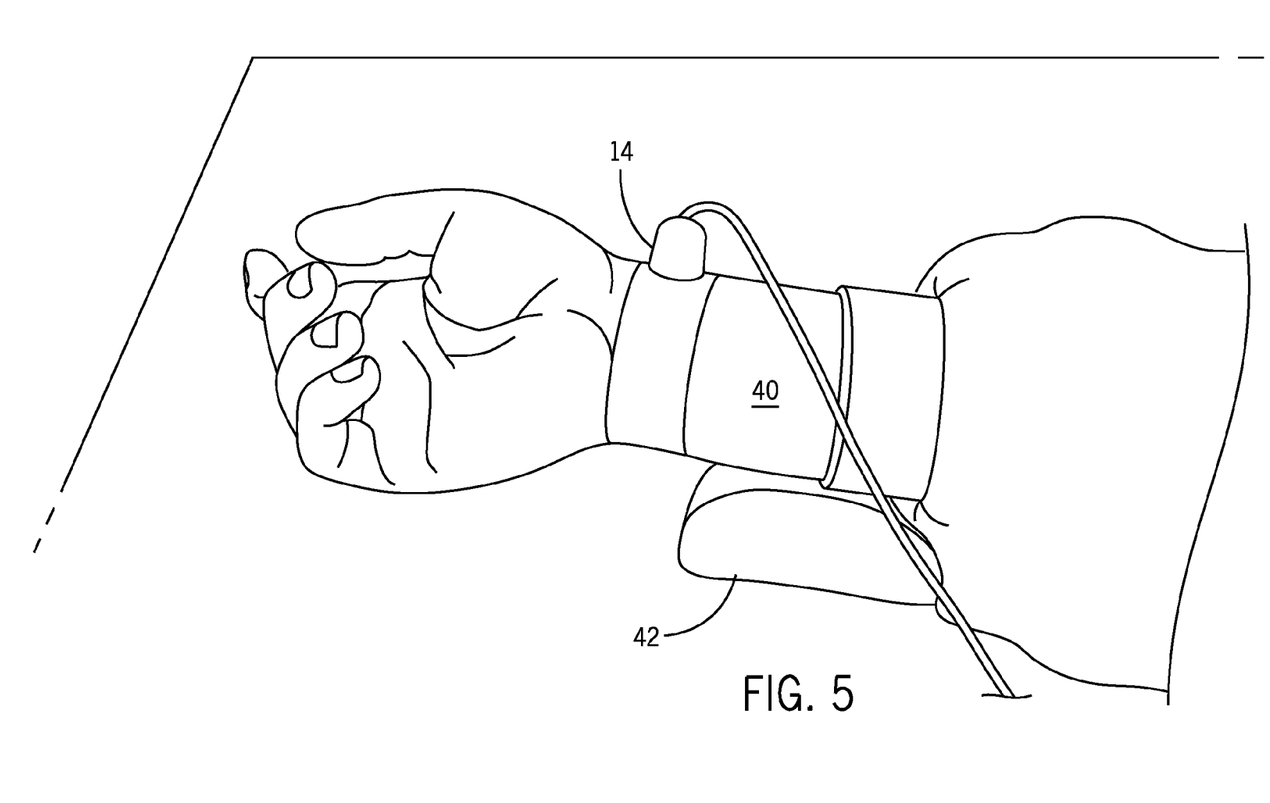
FIG. 5 is a view illustrating the use of a wrist-mounted tonometer in accordance with an embodiment of the invention.

FIG. 5 illustrates a tonometer device 38 which includes a tonometer sensor or transducer 34 attached to a wrist strap 36. As shown in FIG. 5, the strap 36 is preferably wrapped around the patient's wrist 40 so that the face of the tonometer sensor 34 is placed transcutaneously in a fixed location above the radial artery of the patient. Best results are obtained if the wrist is bent outward in the dorsiflex position, which pushes the radial artery towards the surface, thus making it easier to access. When using the dorsiflex position, the wrist 40 should rest on a small cushion 42, as illustrated in FIG. 5. As is known in the art, the pressure of the tonometer against the patient's wrist may have to be adjusted in order to obtain an adequate waveform for the analysis.

Referring again to FIG. 2, the tonometer 34 (or other suitable pressure sensing device such as a suitable brachial cuff device) is attached to the cable 44 which is connected to the signal processing electronics module 32. Analog output cables 46 and 48 are connected between the signal processing electronics module 32 and the personal computer 50. Electrocardiogram data is transmitted in cable 46 whereas peripheral pulse waveform data is transmitted in cable 48. The computer 50 contains an analog to digital converter which receives the analog data in lines 46 and 48 and converts it to digital form. The computer also includes a processing unit, memory, and data storage, as is common in the art. A computer monitor 52 with a screen display is also provided. The computer 50 is programmed with software that displays a trace of the electrocardiogram and the peripheral pulse waveform, and also calculates SPET for each pressure pulse, which is referred to in FIGS. 3 and 4 as the "R-foot interval", as well as trends.

Figure 3:
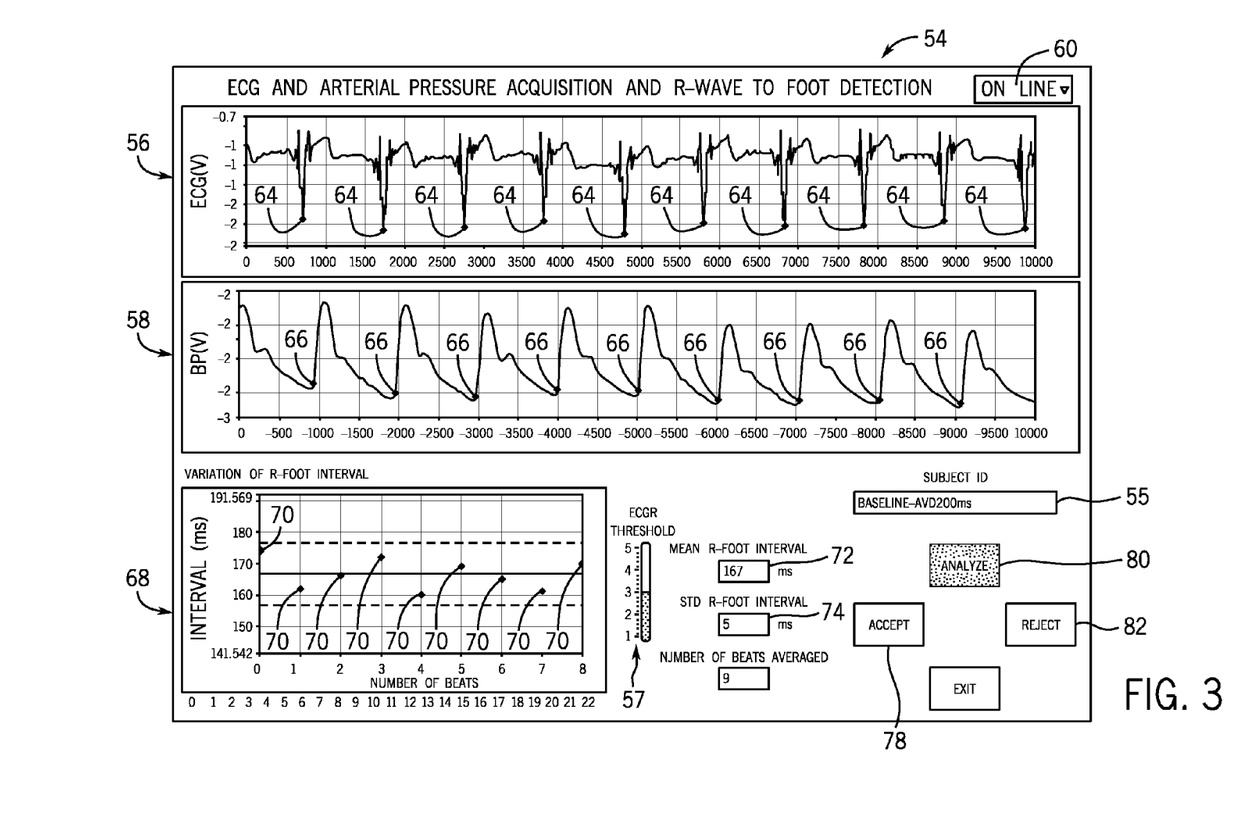
FIG. 3 is a representative screen display on a personal computer in a system implementing the invention.
Figure 4:
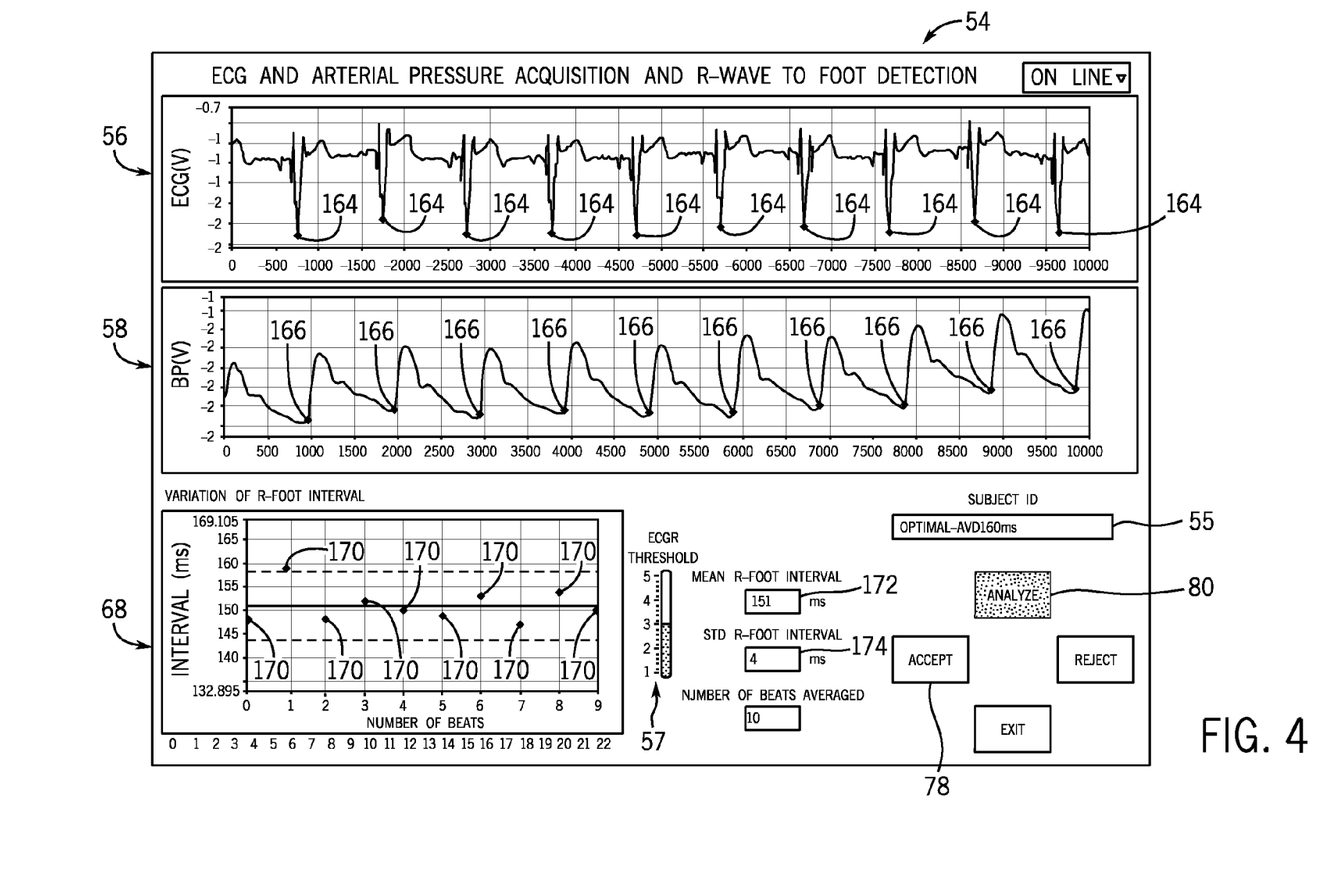

FIGS. 3 and 4 illustrate a computer screen display 54 used to implement the invention. The screen 54 in FIG. 3 contains exemplary data from a patient before CRT optimization. FIG. 4 is similar to FIG. 3; however, the exemplary data is shown for the same patient after CRT optimization. Referring to FIG. 3, patient ID information is entered by the attending staff in box 55 on the screen 54 at the beginning of the session. The screen 54 includes an echocardiogram window 56 and a peripheral pulse waveform window 58. The screen 54 also includes an offline/online button 60. When the system is online and collecting data, the electrocardiogram window 56 displays a trace of the electrocardiogram in real-time, and the peripheral pulse waveform window 58 displays a trace of the peripheral pulse waveform, also in real-time. Note that the time scale for the windows 56 and 58 is in milliseconds so the length of the time axis in the windows 56 and 58 corresponds to a ten second interval, which in the case of FIG. 3, corresponds to roughly nine heart beats. After startup, the attending physician or staff observes the quality of the ECG trace and peripheral pulse waveform trace while the system is online. When the attending staff believes a quality signal has been obtained, the ANALYZE button 80 is selected to stop data acquisition, and the data in windows 56 and 58 remain stationary. FIG. 3 shows the screen at the time at which the ANALYZE button 80 has been selected. At this point, for each respective heart beat, the system in FIG. 3 determines the peak value of the voltage difference in the R-wave for the electrocardiogram 56 and defines the corresponding time as the R-wave impulse time ($T_R$) for the contracting ventricle. In ECG window 56, a dot 64 is illuminated on the electrocardiogram to indicate the time $T_R$ corresponding to the peak value of the voltage difference of the R-wave for each heart beat. Note that the y-axis for the electrocardiogram window 56 is progressively negative from the top to the bottom of the chart. Therefore, the peak value at the R-wave 64 actually appears towards the bottom of the chart.

Also for each respective pulse, the system in FIG. 3 determines the realization of systolic onset in the detected peripheral pulse waveform and defines the corresponding time as a peripherally measured systolic onset time ($T_2$). The system places a dot 66 at the foot of the waveform for each pulse.

Screen 54 in FIG. 3 also includes an interval window 68. The interval window 68 displays the variation of SPET (i.e., $T_2-T_R$=SPET), or the "R-foot Interval", as labeled in FIG. 3, for each heart beat in the ten second trace captured in windows 56 and 58. The "R-foot interval" (SPET) is illustrated by dots 70 in interval window 68. The system preferably calculates the mean and standard deviation of the calculated SPET values 70 and displays these values on the screen, as indicated by reference numerals 72 and 74. If the attending staff is satisfied with the results of the analysis, the accept button 78 is selected and the data is time-stamped and stored. If the staff is not satisfied that the data is reliable, or for some other reason does not desire to store the information, the reject button 82 is selected.

The system and the information on screen 54 is available for use by the attending physician throughout the process of optimizing the programmable settings for the pacemaker. Button 60 can be selected to take the system offline in order to review past results. FIG. 4 illustrates screen 54, with exemplary data for the same patient as in FIG. 3, but taken after the programmable settings for the pacemaker have been adjusted to optimize cardiac performance. In FIG. 4, reference number 164 depicts the peak R-wave value in the electrocardiogram captured after optimization. Reference number 166 represents the foot of the respective pulses in the peripheral pulse waveform taken after optimization. In window 68, dots 170 represent the calculated "R-foot interval" (i.e., SPET) for each of the heart beats for the captured ten second period after optimization. Note that reference number 172 in FIG. 4 indicates that the mean "R-foot interval" (i.e., mean SPET) after optimization is 151 milliseconds as compared to 167 milliseconds before optimization, see reference numeral 72 shown in FIG. 3. Also, the standard deviation, reference number 174, is slightly lower after optimization in this example than before optimization. The attending physician or staff can select the accept button 78 to store this data with a timestamp.

With the invention as described, an attending physician and staff are able to minimize pre-ejection time and presumably isovolumetric contraction time using quantitative data that is collected non-invasively and conveniently. In addition, this data is able to be stored for later use in treating the patient. The accessibility of this data facilitates efficient and faster optimization of pacemaker settings. Those skilled in the art will recognize that the invention is not only helpful to facilitate adjustment of settings for biventricular cardiac pacemakers, but also right side only or left side only cardiac pacemakers.

Figure 6:
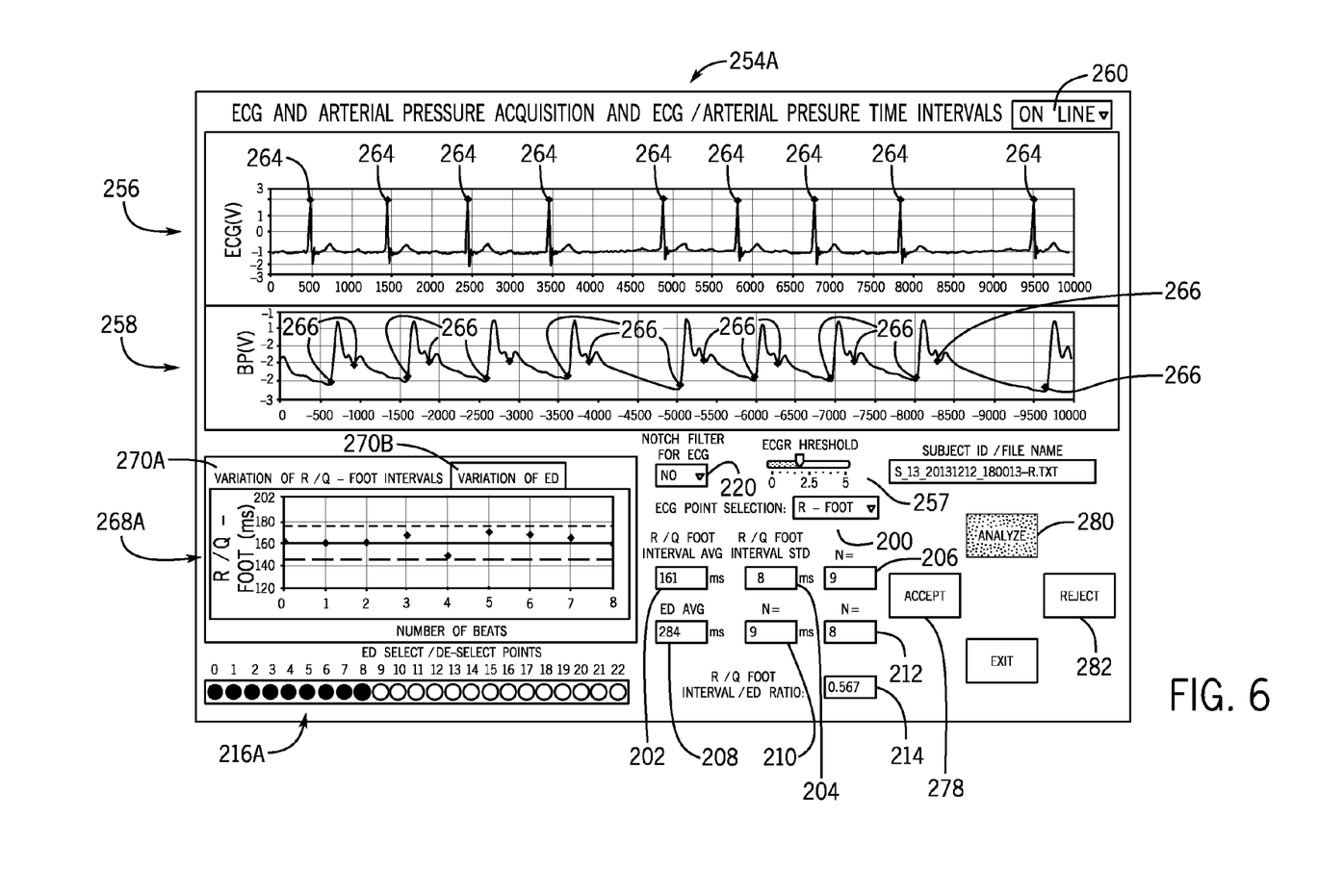
Figure 7:
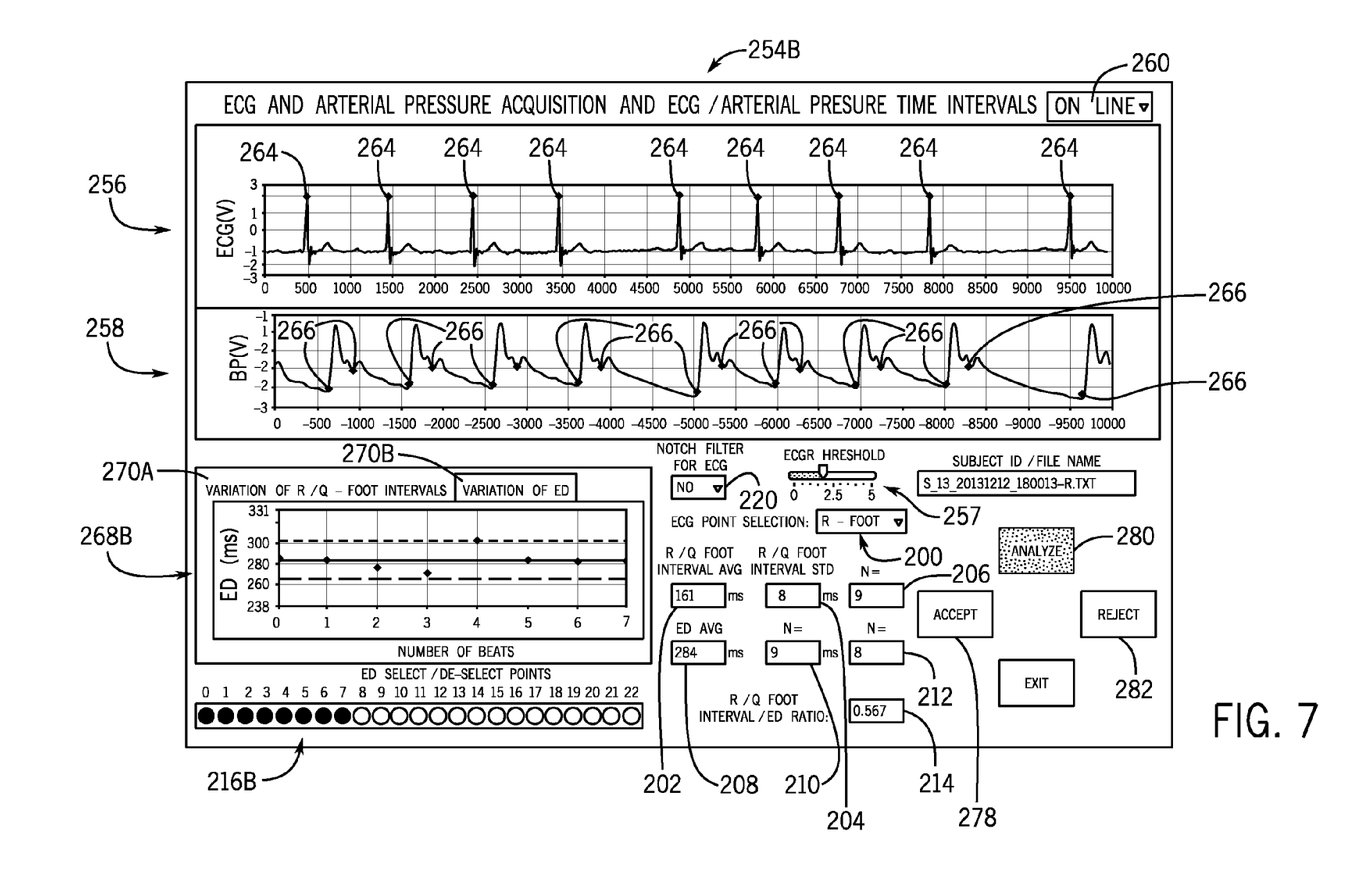
FIG. 7 is a graphical screen display similar to that shown in FIG. 6, showing a graphical display of variation of ED rather than variation of R/Q-foot interval.

FIGS. 6 and 7 are representative screen displays on a personal computer implementing another aspect of the invention. As mentioned, in some circumstances the Q-wave and the QRS complex of the ECG trace is not distinct or not consistent. In these circumstances, a physician may wish to detect the R-wave peak instead of the Q-wave. In addition, some physicians may prefer to use R-wave detection instead of Q-wave detection in all circumstances. Referring to FIG. 6, screen 254A includes menu selection 200 entitled "ECG Point Selection" that enable the physician or staff to select between analyzing the interval between the R-wave peak 264 and the foot 266 of the respective peripheral waveform pulses, or alternatively between the Q-wave as in incorporated U.S. Pat. No. 8,112,150 and the foot of the peripheral waveform pulses. In FIG. 6, the user has selected to use the time interval between the R-wave peak 264 in the ECG trace 256 and the foot 266 of the peripheral waveform pulse 258. The screen 254A is in off line mode 260. The physician is able to toggle between using the R-wave peak and the Q-wave by menu 200. As in the embodiments described in FIGS. 3 and 4, when the system is on line and collecting data, the electrocardiogram window 256 displays a trace of the electrocardiogram in real time, and the peripheral pulse waveform window 258 displays a trace of the peripheral waveform also in real time. FIGS. 6 and 7 show that the Analyze button 280 has been selected and the data accepted by the Accept button 278. The data in FIGS. 6 and 7, in fact, has been stored and is now being displayed in off line mode 260.

The ECG trace 256 in FIG. 6 has been inverted with respect to the ECG scan 256 shown in FIGS. 3 and 4. The ECG trace 256 in FIG. 6 shows a very distinct R-wave and the peak of the R-wave 264 is distinct and relatively easy to detect. The Q-wave in the ECG scan 256 is quite difficult to perceive and would be quite difficult to determine mathematically. This is an example of and ECG trace in which the physician or staff would clearly select to use the R-wave peak instead of trying to identify the Q-wave.

Screen 254A in FIG. 6 also includes a menu selection 220 giving the physician or staff the choice to use a notch filter for the ECG trace. The notch filter would typically be a signal filter for 60 Hz in the United States and 50 Hz in the European Union, the purpose being to eliminate signal noise coming from the power line. In FIGS. 6 and 7, the notch filter 220 has been turned off. As in the previous embodiment, the user can set the ECG R threshold 257 in order to set the sensitivity for determining the location of the R-wave. Reference number 255 refers to the patient ID information box and provides a file name for the data.

Screen 254A also includes interval window 268A. The screen 254A shown in FIG. 6 and 254B shown in FIG. 7 include tabs 270A and 270B to allow the user to select the data that is displayed in the interval window 268A, 268B. In FIG. 6, the user has selected tab 270A entitled "Variation of R/Q-

Foot Intervals", and the window 268A displays the variation of SPET for each heartbeat in the 10-second trace captured in the windows 256, 258. If the user has selected R-Foot via menu 200 then the SPET is defined as $T_2$ minus $T_R$ equals SPET and that value will be displayed. If the user selects Q-foot in menu 200 SPET will be defined as $T_2$ minus $T_0$ equals SPET as described in U.S. Pat. No. 8,112,150. Window 268A therefore provides R-foot intervals for 9 heartbeats. The R-foot interval average for these 9 heartbeats is shown in FIG. 6 as 161 milliseconds, see box 202. There is a line at 161 drawn across window 268A as well. The standard deviation for the R-foot interval is shown to be 8 milliseconds, see box 204. The dashed lines in window 268A show the calculated standard deviation as well. Box 206 on display 254A indicates that these calculations were conducted for 9 heartbeats. Window 216 on FIG. 254A includes radio buttons for selecting or deselecting data points. The physician or staff can decide to eliminate outlier data from the calculation if desired. If this is done then the number of heartbeats (box 206) as well as the interval average (box 202) and standard deviation (box 204).

Screen 254A also displays information pertaining to ejection duration (ED) as calculated from the peripheral pulse waveform as in the prior art SphygmoCor® system. Box 212 indicates that there is sufficient peripheral pulse waveform data in window 258 for 8 heartbeats. Box 208 indicates that the ejection duration (ED) for those 8 heartbeats is 284 milliseconds, in box 10 indicates that the standard deviation is 9 milliseconds. Box 214 displays the ratio SPET divided by ED. The number displayed in box 214 depends on whether the user has selected to use the R-wave peak or the Q-wave in menu 200. Referring to FIG. 7, the information on screen 254B is the same as 254A, except that the user has selected menu option 270B and therefore interval window 268B displays ejection duration (ED) for 8 heartbeats. When the window 268B is selected, the user can select and deselect data points to be used in the calculation of ejection duration, which is then displayed in box 208, 210 and 212.

The foregoing description of the invention is meant to be exemplary. It should be apparent to those skilled in the art that variations and modifications may be made yet implement various aspects or advantages of the invention. It is the object of the following claims to cover all such variations and modifications that come within the true spirit and scope of the invention.

We claim:

1. A method of optimizing one or more programmer settings of a cardiac pacemaker comprising the steps of:
    attending to a patient with a cardiac pacemaker having one or more programmable settings;
    measuring the electrical activity of a heart of the patient in the form of an electrocardiogram which plots a sensed voltage difference between electrodes placed noninvasively in the patient's skin as a function of time, for each pulse of the heart, the electrocardiogram being characterized in part by a QRS complex having an R-wave;
    simultaneously using a sensor to measure a peripheral pulse waveform of the patient as a function of time;
    for each respective pulse, determining from the electrocardiogram the R-wave of the QRS complex and defining a time corresponding to the R-wave as an R-wave impulse time ($T_R$) for a contracting ventricle;
    for each respective pulse, determining the realization of systolic onset in the detected peripheral pulse waveform and defining the corresponding time as a peripherally measured systolic onset time ($T_2$) for the pulse;
    using $T_R$ and $T_2$ to calculate an R-wave surrogate pre-ejection time interval SPET for the pulse;
    presenting information related to the calculated R-wave surrogate pre-ejection interval (SPET); and
    adjusting one or more of the programmable settings for the cardiac pacemaker in an effort to optimize the value of the calculated surrogate pre-ejection time interval SPET for the patient.

2. A method of optimizing one or more programmer settings of a cardiac pacemaker as recited in claim 1 further comprising the steps of:
    for each respective pulse, determining the time ($T_4$) corresponding to the realization of the closing of the aortic valve in the peripheral pulse waveform;
    using $T_4$ and $T_2$ to calculate an ejection duration time (ED) for the patient;
    presenting information relating to the calculated ejection duration time (ED); and
    further adjusting one or more of the programmer settings for the cardiac pacemaker in an effort to optimize the value of the ejection duration (ED) for the patient.

3. A method of optimizing one or more programmer settings of a cardiac pacemaker as recited in claim 2 wherein the determined time $T_4$ for the closing of the aortic valve in the peripheral pulse wave is determined by taking the third derivative of the peripheral pulse wave and identifying the first positive to negative zero crossing following the largest maximum after a second shoulder in the peripheral pulse wave unless a second shoulder cannot be identified, in which case the first positive to negative zero crossing following the largest maximum point of the third derivative after the first shoulder.

4. A method of optimizing one or more programmer settings of a cardiac pacemaker as recited in claim 2 further comprising the step of calculating and displaying the ratio $$\frac{SPET}{ED}.$$

5. A method of optimizing one or more programmer settings of a cardiac pacemaker as recited in claim 1 wherein the settings are adjusted in an effort to minimize the value of the surrogate pre-ejection time interval SPET.

6. A method of optimizing one or more programmer settings of a cardiac pacemaker as recited in claim 1 wherein the step of determining an R-wave impulse time ($T_R$) comprises determining a peak value of the voltage difference in the QRS complex of the electrocardiogram for each respective pulse.

7. A method of optimizing one or more programmer settings of a cardiac pacemaker as recited in claim 1 wherein the peripheral pulse waveform is a radial artery pressure waveform measured by a tonometer.

8. A method of optimizing one or more programmer settings of a cardiac pacemaker as recited in claim 7 wherein the tonometer is strapped to the wrist of the patient in a fixed location to sense the pressure in the patient's radial artery.

9. A method of optimizing one or more programmer settings of a cardiac pacemaker as recited in claim 1 wherein the peripheral pulse waveform is a brachial volumetric waveform measured by a cuff on the patient's upper arm.

10. A method of optimizing one or more programmer settings of a cardiac pacemaker as recited in claim 1 wherein a mean value for the surrogate pre-ejection time interval SPET is calculated as the average difference between the determined R-wave impulse time $T_R$ and the determined peripheral systolic onset time $T_2$ for a series of pulses and is presented.

11. A method of optimizing one or more programmer settings of a cardiac pacemaker as recited in claim 1 wherein the onset of systole in the measured peripheral pulse waveform is determined by analyzing the first derivative of the peripheral pulse waveform and identifying a first negative to positive zero crossing preceding a maximum value for the first derivative.

12. A method of optimizing one or more programmer settings of a cardiac pacemaker as recited in claim 1 wherein the cardiac pacemaker is a biventricular cardiac pacemaker.

13. A system to facilitate optimization of programmable cardiac pacemaker settings during cardiac resynchronization therapy, the system comprising:
a blood pressure sensor adapted to detect a peripheral pulse waveform of a cardiac pacemaker patient;
an electrocardiogram unit having electrodes that are placed on the patient, the ECG unit measuring the electrical activity of the patient's heart in the form of an electrocardiogram which is, for each pulse of the heart, characterized in part by a QRS complex;
a screen display; and
a computer processor programmed with software to implement the following steps:
for each respective pulse on the electrocardiogram, determining the time corresponding to the R-wave of the QRS complex and defining the corresponding time as an R-wave impulse time ($T_R$) for a contracting ventricle;
for each respective pulse, determining systolic onset of the detected peripheral pulse wave and defining the corresponding time as a peripherally measured systolic onset time ($T_2$) for the pulse;
using ($T_R$) and ($T_2$) to calculate a surrogate pre-ejection time interval SPET; and
displaying information on the screen relating to the calculated surrogate pre-ejection time interval SPET.

14. A system as recited in claim 13 wherein the blood pressure sensor is a tonometer.

15. A system as recited in claim 14 wherein the tonometer is mounted to a strap adapted to hold the tonometer against the wrist of a patient in a fixed location to monitor the patient's radial artery.

16. A system as recited in claim 13 wherein the blood pressure sensor is a brachial cuff.

17. A system as recited in claim 13 wherein the computer processor is contained within a personal computer onto which the software is loaded; and the system further comprises a digital signal processing electronic module which is electrically connected to the blood pressure sensor and to leads for the ECG electrodes, and provides analog data for the electrocardiogram and the peripheral pulse waveform that is transmitted to an analog to digital converter which provides digital data in real-time to the personal computer.

18. A system as recited in claim 13 wherein the computer processor is programmed with software to implement the following steps:
for each respective pulse on the electrocardiogram, determining the time corresponding to the Q-wave of the QRS complex and defining the corresponding time as an Q-wave impulse time ($T_0$) for a contracting ventricle;
for each respective pulse, determining systolic onset of the detected peripheral pulse wave and defining the corresponding time as a peripherally measured systolic onset time ($T_2$) for the pulse;
using ($T_0$) and ($T_2$) to calculate an alternative surrogate pre-ejection time interval SPET (Q-wave); and
providing an option for a user to select to display information on the screen relating to the calculated alternative surrogate pre-ejection time interval SPET (Q-wave).

19. A system as recited in claim 13 further comprising a screen display, and further wherein the software displays information on the screen relating to the surrogate pre-ejection time interval SPET.

20. A system as recited in claim 19 wherein the software further analyzes ECG data and peripheral pulse waveform data collected over a fixed time period and calculates averages of the SPET for the heart beats within the fixed time period as well as a standard deviation of SPET for the heart beats in the fixed time period.

21. A system as recited in claim 20 wherein the screen display further comprises a data selection window that enables the user to select or deselect data to be used in calculating an average surrogate pre-ejection time interval SPET for a given time period.

22. A system as recited in claim 13 wherein the personal computer is capable of storing patient electrocardiogram and peripheral pulse waveform data for later analysis.

23. A system as recited in claim 13 wherein the software provides a graphical representation on the screen display of the patient electrocardiogram data and the patient peripheral waveform data, both as a function of time.

24. A system as recited in claim 13 wherein the computer is programmed to determine systolic onset of the detected peripheral pulse waveform by analyzing a first derivative of the peripheral pulse waveform and identifying a first negative to positive zero crossing preceding a maximum value for the first derivative.

25. A system as recited in claim 18 further comprising a screen display, and further wherein the software is capable of displaying information on the screen relating to the surrogate pre-ejection time interval SPET and the alternative pre-ejection time interval SPET (Q-wave).

26. A system as recited in claim 25 wherein the software further analyzes ECG data and peripheral pulse waveform data collected over a fixed time period and calculates averages of the SPET for the heart beats within the fixed time period as well as a standard deviation of SPET for the heart beats in the fixed time period, and further calculates averages of the alternative SPET (Q-wave) for the heart beats within the fixed time period as well as a standard the alternative SPET (Q-wave) for the heart beats in the fixed time period.

27. A system as recited in claim 26 wherein the screen display further comprises a data selection window that enables the user to select or deselect data to be used in calculating an average surrogate pre-ejection time interval SPET for a given time period and alternatively enables the user to select or deselect data to be used in calculating an average alternative SPET (Q-wave) for a given time period.

\* \* \* \* \*